A61F 9/04 | A47G 9/1045 | A47C 31/00 | Y10S 5/911

(12) United States Patent
Bamberg (10) Patent No.: US 10,335,318 B2
(45) Date of Patent: Jul. 2, 2019

(54) LIGHT BLOCKING EYE COVER ATTACHABLE TO A PILLOW

(71) Applicant: Melissa Bamberg, Loomis, CA (US)

(72) Inventor: Melissa Bamberg, Loomis, CA (US)

( * ) Notice: Subject to any disclaimer, the term of this patent is extended or adjusted under 35 U.S.C. 154(b) by 894 days.

(21) Appl. No.: 14/856,404

(22) Filed: Sep. 16, 2015

(65) Prior Publication Data

US 2016/0000607 A1   Jan. 7, 2016

Related U.S. Application Data (63) Continuation-in-part of application No. 12/799,413, filed on Apr. 22, 2010, now Pat. No. 9,138,086.

(51) Int. Cl.
| | |
|---|---|
| *A61F 9/04* | (2006.01) |
| *A47C 31/00* | (2006.01) |
| *A47G 9/02* | (2006.01) |
| *A47G 9/10* | (2006.01) |

(52) U.S. Cl.
CPC .............. *A61F 9/04* (2013.01); *A47G 9/0253* (2013.01); *A47G 9/1045* (2013.01); *A47C 31/00* (2013.01); *Y10S 5/911* (2013.01)

(58) Field of Classification Search
CPC ... A47C 27/086; A47C 21/042; A47C 21/046; A47C 31/00; Y10S 5/911; A61G 7/05738; A61G 7/05746; A61G 7/05753; A61F 9/04
USPC .......................................... 5/655.4, 702, 911
See application file for complete search history.

(56) References Cited

U.S. PATENT DOCUMENTS

| 945,839 | A |   | 1/1910 | Brisbane |
| 1,380,480 | A |   | 6/1921 | Jennings |
| 2,412,769 | A |   | 12/1946 | Easterbrooks |
| 2,413,828 | A |   | 1/1947 | Hirsh |
| 3,459,179 | A | * | 8/1969 | Olesen .................. A47C 27/12 128/889 |
| 3,538,508 | A |   | 11/1970 | Young |
| 3,840,918 | A |   | 10/1974 | Shave |
| 4,420,847 | A |   | 12/1983 | Smith |
| 4,679,263 | A |   | 7/1987 | Honer |
| 4,689,844 | A | * | 9/1987 | Alivizatos ........... A47C 27/086 297/452.16 |
| 4,779,291 | A |   | 10/1988 | Russell |
| 4,843,666 | A | * | 7/1989 | Elesh .................. A47C 27/144 5/723 |
| 4,951,333 | A |   | 8/1990 | Hull |
| 5,127,117 | A |   | 7/1992 | Bridges |

(Continued)

*Primary Examiner* — Robert G Santos
(74) *Attorney, Agent, or Firm* — Heisler & Associates (57) ABSTRACT

An assembly is configured to include an elongate eye covering portion and optionally a pillow portion. The pillow portion includes an enclosure which can contain a pillow therein. The elongate eye covering portion is preferably configured as a sleeve divided into multiple adjacent cells filled with beads or other media. The cells on the sleeve are spaced apart by a distance similar to a spacing between eyes of an adult. Adjacent cells can thus cover eyes and optionally also ears of the user. Seams divide the cells from each other and define a contour of the cells. This contour preferably includes notches between adjacent cells to provide relief for a nose of the user between adjacent cells. Opposite sides of the sleeve can have different heat transfer characteristics so one side feels cooler than the other, allowing selection of a preferred side to contact the wearer.

20 Claims, 4 Drawing Sheets

(56) References Cited

U.S. PATENT DOCUMENTS

| | | | | |
|---|---|---|---|---|
| 5,285,542 | A * | 2/1994 | West | A47C 27/007 |
| | | | | 5/500 |
| 5,572,753 | A | 11/1996 | Ruscitto | |
| 5,618,263 | A * | 4/1997 | Alivizatos | A61F 5/05841 |
| | | | | 128/878 |
| 6,193,740 | B1 | 2/2001 | Rodriguez | |
| 6,363,554 | B1 | 4/2002 | Brown | |
| 6,651,256 | B1 | 11/2003 | Swift | |
| 7,428,763 | B2 | 9/2008 | Hightower | |
| D583,605 | S | 12/2008 | Krinsky | |
| 7,601,168 | B2 | 10/2009 | Koby | |
| 7,657,954 | B1 | 2/2010 | Bunkers | |
| 7,818,841 | B2 * | 10/2010 | Happel | A47C 21/046 |
| | | | | 5/655.4 |
| 8,239,987 | B2 | 8/2012 | Sharp | |
| 8,887,333 | B2 | 11/2014 | Cohen | |
| 9,138,086 | B1 * | 9/2015 | Bamberg | A47G 9/10 |
| 2008/0034503 | A1 | 2/2008 | Hightower | |
| 2008/0216244 | A1 | 9/2008 | Minton | |
| 2009/0019642 | A1 * | 1/2009 | Happel | A47C 21/046 |
| | | | | 5/655.3 |
| 2010/0301655 | A1 | 12/2010 | Mezger | |
| 2012/0144590 | A1 | 6/2012 | Sharp | |
| 2012/0186016 | A1 | 7/2012 | Martin | |
| 2012/0210516 | A1 | 8/2012 | Popovic | |
| 2013/0227784 | A1 | 9/2013 | Holliday | |
| 2013/0312180 | A1 | 11/2013 | Moran | |
| 2013/0312192 | A1 | 11/2013 | Lee | |
| 2014/0000036 | A1 | 1/2014 | Cohen | |
| 2014/0199507 | A1 | 7/2014 | Moran | |
| 2016/0000607 | A1 * | 1/2016 | Bamberg | A47G 9/1045 |
| | | | | 2/15 |
| 2016/0120253 | A1 | 5/2016 | Schenk | |
| 2018/0008468 | A1 * | 1/2018 | Bamberg | A47G 9/0253 |

\* cited by examiner

Fig. 1

LIGHT BLOCKING EYE COVER ATTACHABLE TO A PILLOW

CROSS-REFERENCE TO RELATED APPLICATIONS

This application is a continuation-in-part of U.S. patent application Ser. No. 12/799,413, filed on Apr. 22, 2010.

FIELD OF THE INVENTION

The following invention relates to pillows for supporting a head of a user while sleeping or resting. More particularly, this invention relates to pillow accessories attachable to a pillow or pillow containing structure which enhance the sleep experience by at least partially blocking light and/or sound experienced by the user.

BACKGROUND OF THE INVENTION

As individuals spend approximately one-third of their lives sleeping, optimization of the sleep experience can have significant benefits for an individual. While conditions for optimizing a sleep experience vary from individual to individual, generally it is desirable to have a comfortable physical posture in a prone position lying upon a bed or other underlying support structure having a desired amount of firmness/softness and a desired amount of conforming shape to the user's body.

Perhaps the most important portion of the underlying support for the user during sleep is the pillow for supporting the head of the user. Pillows vary in dimensions, as well as degree to which they conform to the head of the user. Once an optimal pillow has been identified by an individual, the individual will often keep the pillow for a long period of time, potentially even taking the pillow with the individual on trips, so that sleep away from a home location can to some extent match the sleep experience enjoyed at home.

Typically, the pillow used by the individual is covered by some form of case. The case beneficially allows for frequent washing so that clean fabric is presented against the user's head without requiring frequent washing of the pillow itself. While pillows are known to have a variety of different shapes and contours, perhaps the most common shape for a sleep pillow is a rectangular form with a width approximately fifty percent greater than a height. Longer edges of the pillow can generally be referred to as sides while shorter edges of the pillow can generally be referred to as ends. A typical pillow case has closed sides as well as one closed end. A second end is typically open to allow the pillow to be easily inserted and removed from the case.

The sleep experience is often further enhanced by minimizing light striking the sleeping individual, and minimizing noise experienced by the sleeping individual. Even with eyes closed, excessive light striking the eyelids of the individual penetrate through the eyelids to some extent and tend to stimulate the vision center of the brain, often resulting in disruption of sound sleep. Similarly, excessive noise can stimulate the auditory center of the brain and provide excessive stimulation to the brain to disrupt sound sleep. Accordingly, it is known in the prior art to provide sleep aides in the form of light blocking and sound blocking equipment. Such equipment is particularly desirable when it is not possible to effectively control light and noise within a sleeping room.

One form of common light blocking sleep aide is a "sleep mask." Such a sleep mask is generally in the form of a small pillow of material shaped to rest over the eyes of the user. Some form of strap is typically attached to ends of the small pillow with the strap long enough to gird about the head of the user. The strap thus holds the eye pillow in place over the eyes of the user. The eye pillow is typically formed of a soft material which is also sufficiently opaque to block substantially all light from passing through the eye pillow.

While the sleep mask is generally effective overall in blocking light striking the eyes of the sleeping individual, sleep masks do have some drawbacks. The strap must pass around the head of the sleeping individual, presenting the potential for tangling with the hair of the individual or otherwise providing excessive tactile stimulation to the individual which can then stimulate tactile sensory centers of the brain and disrupt the sleep experience. Furthermore, such sleep masks present a separate object which must be stored and then accessed when needed for convenient use.

Often an individual is not fully aware of the need of the sleep mask when first going to sleep. Hours later, when the sun comes up and strikes the sleeping individual, the sleeping individual desires to continue to sleep but needs to block light striking the user's eyes. The user must then find and don the sleep mask for it to be effectively utilized. If this process is too complex, the process of putting on the sleep mask will itself awaken the individual to the point where it may be difficult to again achieve sound sleep. Even if the sleep mask is already present adjacent the sleep area, such as resting on a nightstand adjacent the sleeping individual, the sleeping individual must still place the sleep mask over the user's eyes and position the strap about the user's head before going back to sleep. Such a process typically at a minimum requires opening of the user's eyes to find the sleep mask and a not insignificant amount of fiddling with the strap before the sleep mask is in the desired position. Accordingly, a need exists for a light occluding structure which can be more readily deployed when needed by an individual, even with eyes closed and maintaining a quasi-sleeping or barely awake state, so that return to sound sleep can most effectively be achieved.

Prior art equipment also exists to minimize sound sensed by a sleeping individual. For instance, ear plugs are commonly known which can be placed within the ears of the individual to block sound experienced by the individual while sleeping. Similarly, noise canceling headphones are known which can passively and actively act to minimize sound passing to the ears of the individual. Such sound blocking equipment, while generally effective, shares many of the drawbacks experience by sleep masks in that once the sound blocking equipment is required, the user typically must awaken sufficiently to find and deploy the sound blocking equipment for it to be effective, with such activity typically disrupting the sleep experience.

Accordingly, a need also exists for a sound blocking system which can be readily deployed by an individual in a quasi-sleeping or barely awake state. Most preferably, such a system would be capable of deploying both light blocking and sound blocking equipment simultaneously in such an easy fashion that the user could truly remain sleeping, or only barely awaken before achieving effective light and sound blocking and resumption of a sound sleeping experience.

SUMMARY OF THE INVENTION

With this invention, a device is provided which blocks eyes of a user from light, and potentially also sound, which is attached to a pillow assembly, or at least provides an enclosure for a pillow assembly so that the light blocking structure is readily available adjacent the pillow whenever needed by the user. In a preferred embodiment, the apparatus includes a pillow enclosure which is configured to have a hollow interior sized and shaped to receive the user's pillow therein. Typically, this enclosure would be closable, such as with a zipper, to completely conceal the user's pillow therein. While the enclosure could double as a pillowcase, most preferably the pillow enclosure is separate from the pillowcase and a separate pillowcase is provided overlying this enclosure.

An elongate eye covering structure is attached to this enclosure or other pillow assembly, or provided separate from the pillow enclosure or assembly. This eye covering structure is preferably in the form of a sleeve having a hollow interior. This hollow interior is divided into separate cells which extend linearly from a proximal end of the sleeve where the sleeve attaches to the pillow enclosure, to a distal end opposite the proximal end. Each of the cells is typically separated merely by stitching to divide the sleeve into separate cells. Media is provided within each cell, such as in the form of beads, beans or other small solid media, with the interiors only partially filled so that the cells can readily be flexed into a contour matching a contour of the user's face overlying eyes of the user. Most preferably, more than two such cells are provided with the spacing between the cells similar to a spacing between eyes of a typical adult. With such a spacing, some cells can readily be provided overlying ears of the user while other cells can be readily provided overlying eyes of the user. Thus, the same sleeve portion can simultaneously cover both eyes and ears of the user.

With the sleeve attached to the pillow assembly, when a user desires to block noise or light, such as when awakening from a deep sleep to a lower level of sleep or barely awake state, the user can readily find (even without opening the user's eyes) the sleeve at the end of the pillow assembly and place the sleeve assembly over the user's eyes (and optionally also ears). Sound sleep can then be readily resumed with a minimum of light and/or sound interfering with the sleep experience.

In one embodiment the pillow assembly has at least two sleeve portions extending from separate portions thereof. In such an arrangement multiple sleeves can be simultaneously utilized by a single user, or two sleepers adjacent each other can each benefit from one of the two sleeves, or a user can have the highest degree of confidence that a sleeve will always be found when reaching to either end of the pillow assembly.

In another embodiment, the sleeve is provided alone, without the pillow enclosure or other pillow assembly. In such an arrangement, the sleeve can be beneficially used with or without a pillow. One such sleeve could have distinct fabric or other material on opposite sides and having distinct heat transfer characteristics and/or textures. In this way, a user can beneficially place a side that feels hotter or feels colder against the user's eyes and face to provide maximal comfort. Similarly, a preferred texture can be selected and oriented adjacent to the user's face. As an option, at least one end cell can be provided slightly longer and optionally empty of media to facilitate tucking in and holding of the sleeve in place. In other variations, such empty end cells can be omitted to simplify the invention.

OBJECTS OF THE INVENTION

Accordingly, a primary object of the present invention is to enhance the sleep experience by providing a pillow assembly which includes an eye covering structure attached thereto.

Another object of the present invention is to provide a method for enhancing the sleep experience by allowing a user to readily cover the user's eyes and/or ears without fully awakening.

Another object of the present invention is to provide an eye cover which is attachable to a pillow and which can be readily deployed over eyes of the user to block light striking the user.

Another object of the present invention is to provide an eye cover which is formed of soft flexible material which can comfortably conform to eyes and adjacent facial structures of the user.

Another object of the present invention is to provide an elongate flexible structure which can cover both eyes and ears of a user during sleep, and which is attachable to a pillow assembly.

Another object of the present invention is to provide an eye covering structure attachable to a pillow which can accommodate pillows of a variety of different sizes and shapes so that the benefits of the eye covering structure can be enjoyed along with the most preferred pillow of the user.

Another object of the present invention is to provide an eye covering structure which can be readily washed when needed.

Other further objects of the present invention will become apparent from a careful reading of the included drawing figures, the claims and detailed description of the invention.

DESCRIPTION OF THE PREFERRED EMBODIMENT

Figure 1:
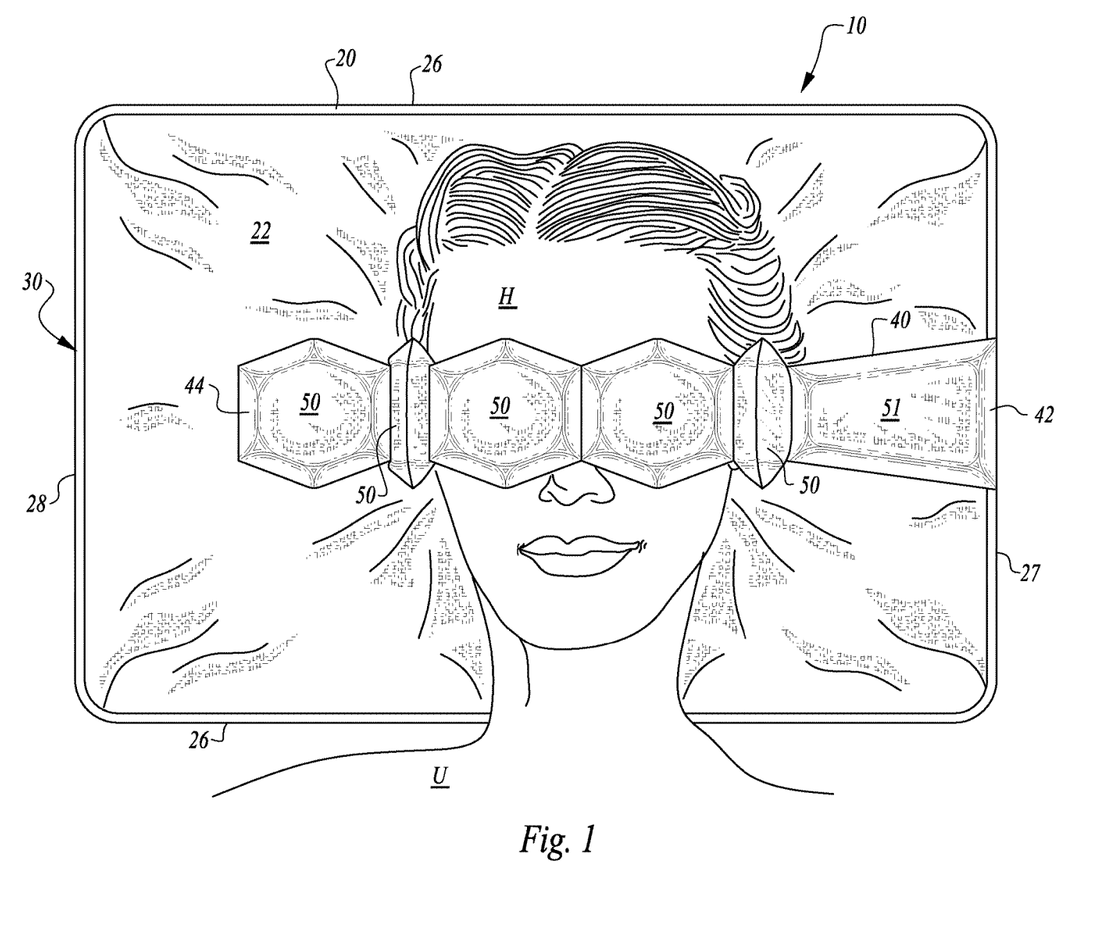
FIG. 1 is a top plan view of the light blocking eye cover attachable to a pillow according to a preferred embodiment of this invention and shown underlying a head of a user, and with a pillowcase most typically also utilized, but not shown for clarity in demonstrating this embodiment of the invention.

Referring to the drawings, wherein like reference numerals represent like parts throughout the various drawing figures, reference numeral 10 is directed to an assembly (FIGS. 1-3) defining a preferred embodiment of a light blocking eye cover attachable to a pillow P according to this invention. A user U rests the user's head H on a pillow enclosure 20 with a sleeve 40 portion having cells 50 therein resting over eyes of the user U. The cells 50 block light directed toward eyes of the user U and promote sound sleep for the user U.

In essence, and with particular reference to FIGS. 1-3 and 6, basic details of the assembly 10 of this invention are described according to a preferred embodiment. In this preferred embodiment, an enclosure 20 is provided with a hollow interior 35 accessed through an opening 30 to support a pillow P therein. A sleeve 40 or other elongate eye cover is coupled to the enclosure 20 and extends from an end of the enclosure 20 in an elongate fashion. This sleeve 40 includes a plurality of separate cells 50 therein. Each of the cells 50 are spaced apart by a distance similar to a spacing between eyes of the user U. Beads 60 or other media are located within an interior 56 of each cell 50. The cells 50 can thus conform to portions of the head H of the user U surrounding the eyes to block light directed toward to the user U.

Figures 2, 3, 6:
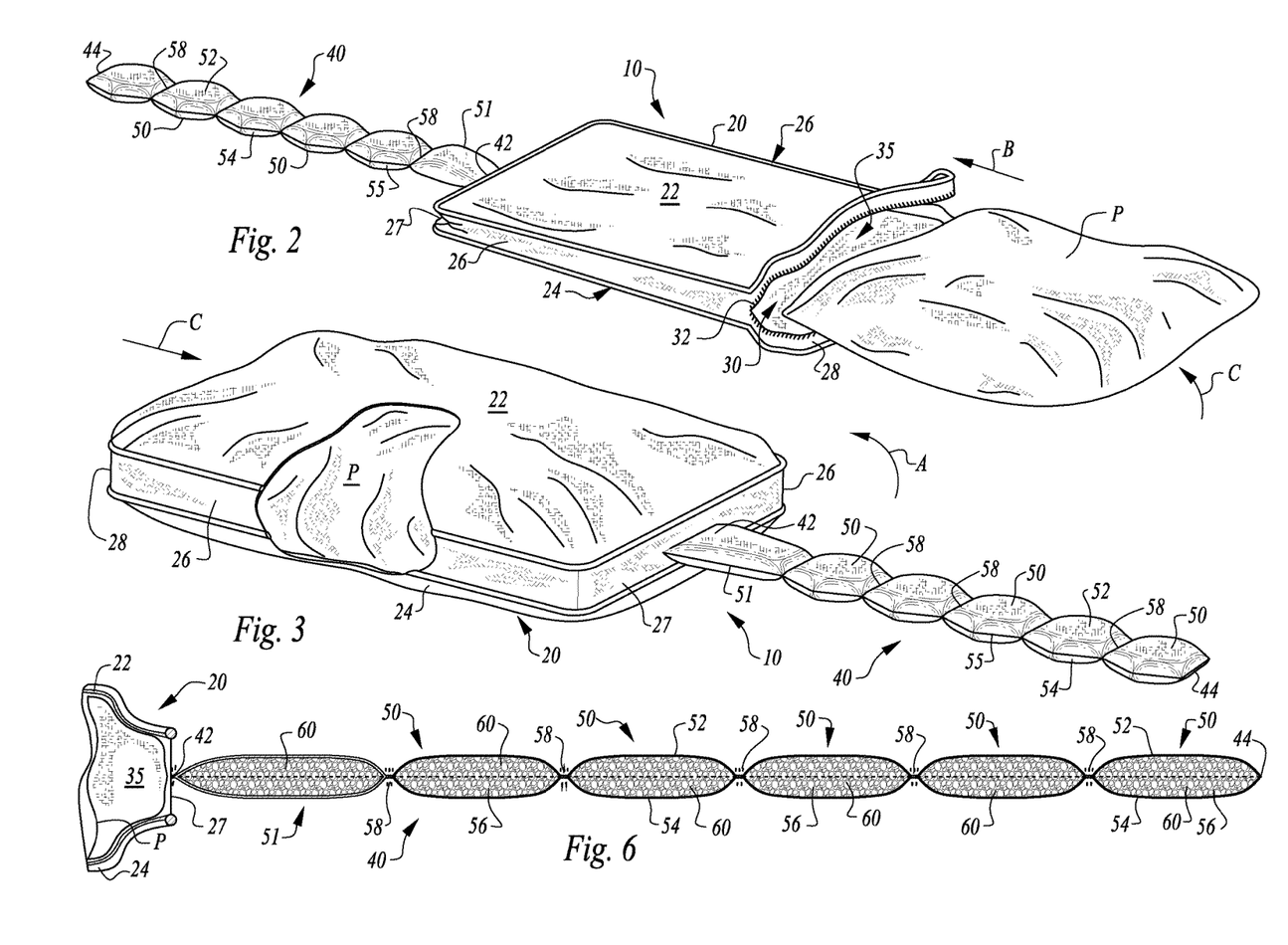
FIG. 2 is a perspective exploded parts view of that which is shown in FIG. 1 with a pillow exploded out of an enclosure portion of the invention and with a sleeve portion shown extending linearly away from the pillow enclosure portion of the invention.
FIG. 3 is a perspective view similar to that which is shown in FIG. 2 but from a reverse angle and with portions of the pillow containing enclosure cut way to reveal the pillow therein.
FIG. 6 is a sectional view taken along lines 6-6 of FIG. 4 and revealing interior contents and structures for the sleeve portion of the invention according to this embodiment.
Figures 4, 5, 7:
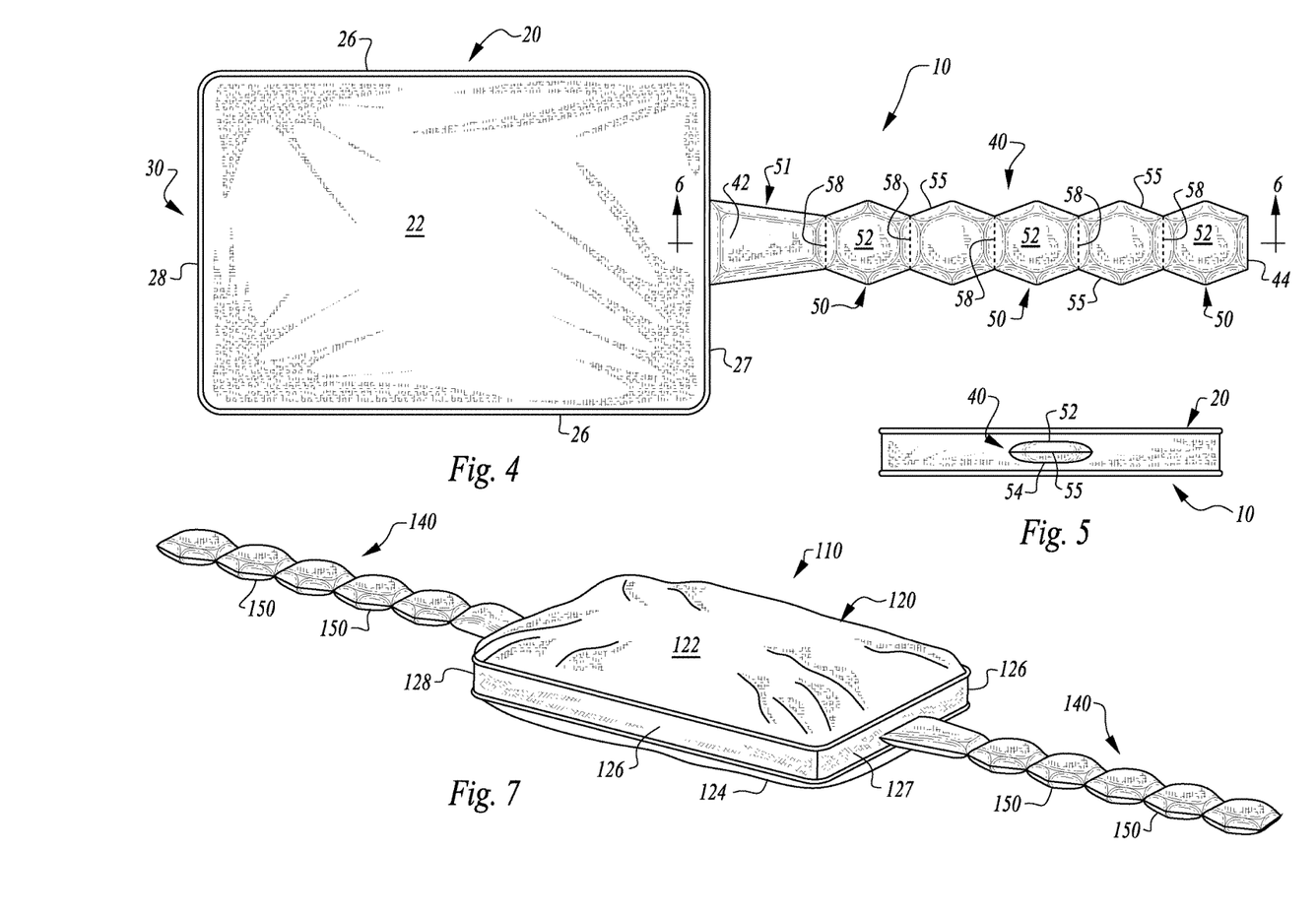
FIG. 4 is a top plan view of that which is shown in FIG. 3.
FIG. 5 is an end elevation view of that which is shown in FIG. 3.
FIG. 7 is a perspective view of an alternative embodiment of this invention featuring two separate elongate eye covering structures extending from opposite ends of a pillow containing enclosure.

More specifically, and with particular reference to FIGS. 2-4, details of the enclosure 20 of the assembly 10 are described, according to this most preferred embodiment. The enclosure 20 provides a preferred form of a pillow portion of this invention. In different embodiments, this pillow portion can include both the enclosure 20 and the pillow P, or only the enclosure 20. It is also conceivable that the enclosure 20 and the pillow P could be integrated together into a single unit. As another alternative, a pillowcase could be provided separate from the pillow portion or be a third part of the pillow portion. The enclosure 20 could also be configured as a form of pillowcase resting over the pillow P.

In this most preferred embodiment, the enclosure 20 is provided separate from the pillow P and separate from a pillowcase that would be positioned overlying both the pillow P and the enclosure 20. This enclosure 20 includes a top surface 22 opposite a bottom surface 24. These surfaces 22, 24 are preferably of similar size and shape and are spaced apart by an interior 35 of the enclosure 20. The surfaces 22, 24 are joined together at opposite long sides 26. The surfaces 22, 24 are also joined together at the first end 27. A second end 28 of the enclosure 20 opposite the first end is preferably substantially open and not joining the surfaces 22, 24 together.

The first end 27 preferably supports the sleeve 40 or other elongate eye covering structure of this invention. The second end 28 provides access for the pillow P (along arrow B of FIG. 2). The surfaces 22, 24 are formed of flexible fabric material and are preferably sized similar to a contour of the pillow P to be contained within the enclosure 20. The sides 26 preferably have a height which further accommodates a volume of the interior 35 for containment of the pillow P within the enclosure 20. While the surfaces 22, 24 could be attached directly together, most preferably the sides 26 have a separate panel joining the surfaces 22, 24 in a manner spaced by this additional panel. This additional panel can extend entirely around the enclosure 20 perimeter in a most preferred embodiment.

An opening 30 is preferably provided on the second end 28. This opening 30 is preferably sufficiently large to allow the pillow P to easily pass into the interior 35 through the opening 30 (along arrow B of FIG. 2). A closure is preferably provided on the opening 30, such as in the form of a zipper 32. Buttons, snaps or other closure elements could similarly be utilized. As another alternative, the opening 30 could merely be left open with the pillow P generally tending to remain within the enclosure 20 due to typical friction and gravity forces.

With particular reference to FIGS. 3-6, details of the sleeve 40 are described according to this preferred embodiment. The sleeve 40 defines a preferred form of elongate eye covering structure for this invention. While the sleeve 40 in this preferred embodiment is configured as a hollow tube of flexible fabric, it is conceivable that other forms of elongate eye covering structures could be utilized, such as a single elongate piece of fabric rather than a tube. By configuring the elongate eye covering structure in the form of a sleeve 40, media 60 can readily be placed inside the sleeve 40 and the media, such as beads 60 can be isolated into separate cells 50 by providing divider seams 58 perpendicular to a long axis of such a sleeve 40.

With the sleeve 40 of this preferred embodiment, the sleeve 40 is preferably directly attached to the enclosure 20, such as at the second end 28, by stitching a proximal end 42 of the sleeve 40 directly to the second end 28 of the enclosure 20. A distal end 44 is provided opposite the proximal end 42 and defines a portion of the sleeve 40 most distant from the enclosure 20. As an alternative, the sleeve 40 could be coupled to the enclosure 20 through an intervening structure or structures. Such coupling is permanent in this embodiment, but could be removably attachable, such as by use of a fastener (e.g. buttons, snaps, ties, zippers, hook and loop fasteners, etc.).

The sleeve 40 is preferably formed of flexible fabric of sufficiently tight weave to keep the beads 60 or other media contained within the interior 56 of the cells 50 formed within the sleeve 40. Most preferably, this material forming the sleeve 40 is sufficiently soft to be comfortable when placed adjacent and touching the head H of the user U adjacent eyes of the user U. Such comfortable suitable materials can include velvet, satin, silk and other soft flexible materials.

Most preferably, the material forming the sleeve 40 is also substantially opaque so that minimal light passes through the sleeve 40, or other elongate light blocking structure, even when high intensity light is directed toward the head H of the user U.

Preferably, the sleeve 40 is divided into separate cells 50. These cells 50 are preferably each similar in size and shape, except for a first cell 51 closest to the enclosure 20. This first cell 51 would typically not be utilized because it is too close to the enclosure 20, and with the user's head resting on the enclosure 20 containing the pillow P, it can be difficult to place this first cell 51 in a position overlying eyes or ears on the head H of the user U. Thus, this first cell 51 could conceivably be configured without any beads 60 therein, and sized and shaped differently from the other cells 50.

The remaining cells 50 could have differing sizes and shapes, but most preferably are each of similar size and shape. In particular, each cell 50 preferably includes an upper side 52 opposite a lower side 54 which are of similar size and shape and are formed by portions of the sleeve 40. This shape is preferably approximately hexagonal in form with two of the sides of the hexagon formed by divider seams 58 dividing the adjacent cells 50 from each other. Edge seams 55 would define the other four sides of such a hexagonal structure. With such a configuration, each divider seam 58 would also be adjacent a small notch between adjacent cells 50. This notch is conveniently provided to allow a nose of the user U to have some relief when adjacent cells 50 are resting over eyes of the user U. While such notches could conceivably be provided only on one side of the sleeve 40, preferably such notches are provided on both sides of the sleeve 40 so that the cells 50 have a symmetrical appearance and for maximizing flexibility of use.

A size of the cells 50 is preferably such that centers of two adjacent cells are spaced apart a distance similar to an average spacing between eyes of an adult human. This distance is also typically close to a distance between a left eye and a left ear of an adult human and a distance between a right eye and a right ear of an adult human. Thus, when adjacent cells 50 are resting over eyes of the user U, further adjacent cells 50 can reside over ears of the user U. Thus, four adjacent cells 50 can sequentially cover a left ear, left eye, right eye and finally right ear of the user U (see FIG. 1). In such a configuration, the user U experiences both reduced exposure to light and sound to maximize the sleep experience.

The upper sides 52 and lower sides 54 are joined together at the edge seams 55. These edge seams 55 are preferably not straight, but rather follow a contour which causes the cells 50 to have the hexagonal shape described above. As an alternative, the edge seams 55 could have a variety of different configurations, either to increase a size of the notches between adjacent cells 50, or to eliminate such notches. While the cells 50 preferably have a faceted appearance along the edge seams 55 and divider seams 58, it is conceivable that the cells 50 could have a more rounded appearance, such that the cells 50 appear to be approximately circular.

The interiors 56 of the cells 50 are filled with beads 60 or other media. These beads 60 are preferably solid small beads of plastic material such as that utilized commonly in stuffed animals (e.g. polyethylene). Other forms of media could similarly be utilized, such as beans of various different sizes which have been dried (or rice or other grains or seeds). Furthermore, it is conceivable that the cells 50 could be stuffed with cotton or other fibrous filler material.

Most preferably, beads 60 are utilized which have some degree of weight which tends to cause the cells 50 to remain where positioned and apply light pressure to the eyes of the user U. Such weighting of the cells 50 with the media 60 can enhance the sleep experience by taking advantage of the concept of "pressure touch" which has been shown to increase Dopamine release within the brain and Nerve Growth Factor release, as well as a parasymphatetic response, all of which are productive in enhancing the sleep experience.

While the beads 60 provide a preferred form of weighting for the cells 50, the cells 50 could be weighted by utilizing a heavier weight fabric, or be weighted with other materials, which could conceivably even include liquid materials, such as a liquid or gel-like material encapsulated within a vapor proof enclosure inside each cell 50.

While the assembly 10 preferably includes a single sleeve 40, an alternative assembly 110 can be utilized (FIG. 7) which includes two such sleeves 140. In such a configuration, an alternative enclosure 120 has a top surface 122 opposite a bottom surface 124 and with sides 126 extending between the surfaces 122, 124. Uniquely, both a first end 127 and a second end 128 would include a sleeve 140 extending therefrom. Each sleeve 140 would include multiple cells 150 therein similar to the cells 50 of the first embodiment identified above.

In the embodiment of the assembly 110, the enclosure 120 can include an opening formed within one of the sides 126, or an opening can be provided above or below one of the sleeves 140 and on either the first end 127 or the second end 128. In such an embodiment, the enclosure 20 could double as a pillowcase. As another alternative, a customized pillowcase could be provided which includes a slot on at least one end thereof which allows the sleeve 140 to pass through such a slot and still allow the pillowcase to rest over the enclosure 20.

While the sleeves 40, 140 have been described as being formed of a material which is comfortable when in direct contact with skin of the user U, it is conceivable that a separate cover could be provided for the sleeve 40, 140 itself. Such a sleeve case would have a form generally matching that of the sleeve 40, 140 and could then be removable, such as for washing separate from the sleeve 40, 140.

When the assembly 10 is in use, the user U would lie down with the head H of the user U resting upon the pillow P, with the pillow P contained within the enclosure 20, and typically with a pillowcase overlying the enclosure 20, so that the head H of the user U is actually in contact with the pillowcase. Such a pillowcase could be placed over the enclosure 20 by passage of the pillowcase along arrow C (FIGS. 2 and 3) to cover the entire assembly 10 except for the sleeve 40.

Once the head H of the user U is resting upon the pillow P, the sleeve 40 is rotated (along arrow A of FIG. 3) until cells 50 of the sleeve 40 are resting over either eyes, ears or both of the user U. Because the sleeve 40 is attached to the enclosure 20, the user U does not need to fully awaken and open the user's eyes to find the sleeve 40 and associated cells 50. Rather, in a barely awake state the user U can use the user's hands to feel for the ends of the pillow, grab the sleeve 40 and position cells 50 of the sleeve 40 over eyes and/or ears of the user U. The user U can then resume a deep sleep state while light and/or sound stimulation has been diminished. In such a fashion, this invention facilitates an optimal sleep experience.

Figures 8, 9:
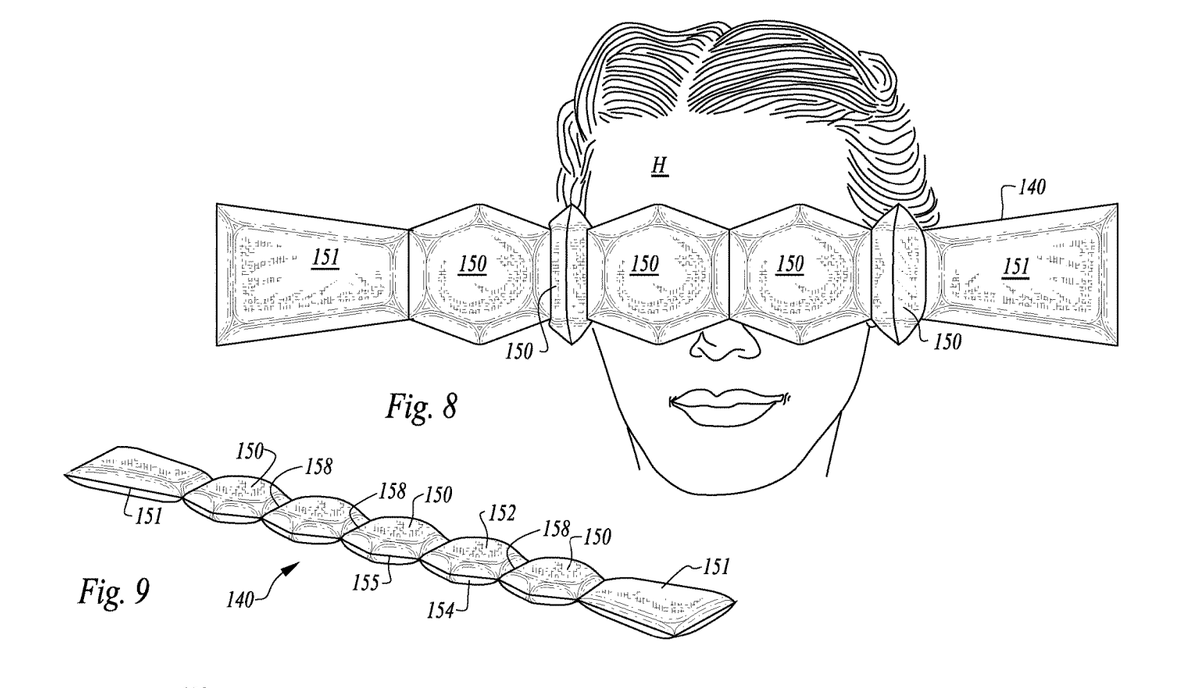
FIG. 8 is a perspective view of an alternative embodiment sleeve of this invention usable without a pillow or pillowcase to cover eyes and optionally also ears of a wearer.
FIG. 9 is a perspective view of the sleeve depicted in FIG. 8.
Figure 10:
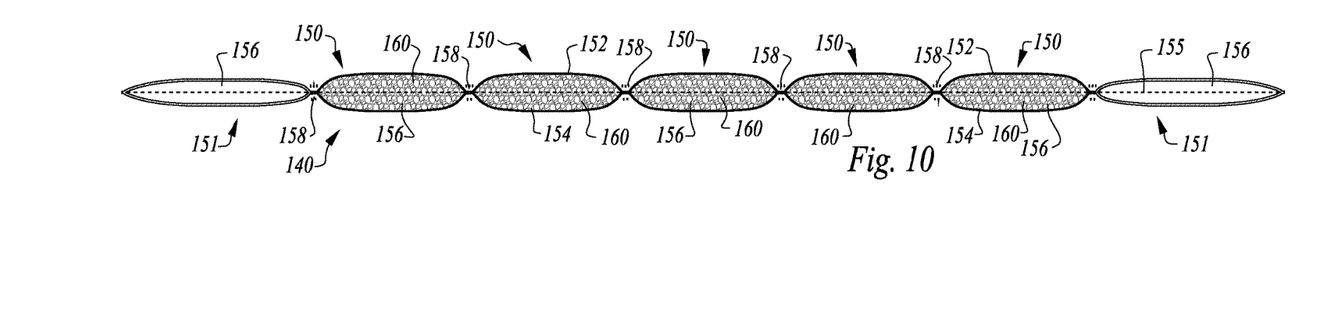
FIG. 10 is a full sectional front elevation view of that which is shown in FIG. 9, revealing interior details of the sleeve of FIG. 8.

With particular reference to FIGS. 8-10, details of an alternative sleeve 140 are described. The sleeve 140 is distinct from the sleeve 40 (FIGS. 1-7) in that it is provided separate from a pillow or pillowcase. The sleeve 140 includes a series of cells 150 spaced from each other in a manner similar to the cells 50 of the assembly 10 (FIGS. 1-7). Thus, the cells 150 include a series of similar cells ending at end cells 151 adjacent a proximal and distal end (or more generally described as first and second ends) of the sleeve 140.

End cells 151 adjacent the proximal and distal ends preferably are empty rather than being filled with beads 160 of media as are the other cells 150. The end cells 151 are also preferably longer and somewhat trapezoidal in shape as shown. This facilitates tucking of the proximal or distal cells (or both) beneath a head H of a wearer while central cells 150 rest over eyes (and optionally also ears) of the wearer. In a simpler embodiment, the empty end cells 151 could be omitted so that all of the cells 150 would be filled with beads 160 of media and similar in shape.

The cells 150 are separated from each other by divider seams 158 and in one embodiment an edge seam 155 (or pair of edge seams 155) join an upper side 152 to a lower side 154 to provide the structure of the sleeve 140. Interiors 156 of each cell 150 are filled with beads 160 of media (except for the end cells 151 which are preferably empty).

The upper side 152 and lower side 154 are most preferably formed of distinct materials. These distinct materials are selected so that they have distinct heat transfer properties. Thus, one of the sides will tend to have a warmer feel to a wearer and the other side will tend to have a cooler feel for the wearer. The wearer can thus select the side for contact with the face of the wearer which provides the most comfort. The distinct heat transfer properties can be in the form of distinct coefficients of heat transfer for the fabrics or other materials forming these sides 152, 154, or can be in the form of the fabrics or other materials forming the sides 152, 154 having distinct heat capacities (or some combination of both). Furthermore, a different apparent heat transfer characteristic could be provided to the sides 152, 154 by providing a distinct texture for the fabric or other material forming the sides 152, 154.

To provide a different apparent temperature for the opposite sides of the sleeve 140, another option is to provide one of the fabrics or other materials forming the sides being more porous than the other fabric, so that the increased or decreased porosity has an apparent temperature difference for the wearer.

To ensure that the adjacent cells 150 can conveniently reside over each eye of a wearer, the spacing between centers of adjacent cells 150 preferably correspond somewhat to an average interpupillary distance for a typical adult human. Such an average interpupillary distance has been shown in at least one study of U.S. military personnel (male and female) to be approximately 63.5 millimeters. However, different individuals can tend to have different interpupillary distances straying from this average somewhat. To accommodate most adult individuals a spacing between about 60 millimeters and about 70 millimeters is one arrangement for adjacent cells 150.

In one embodiment the cells are spaced further than the average interpupillary distance to accommodate placement of cells 150 over ears of the wearer as well as over eyes of the wearer. For instance, a series of four adjacent cells can be configured with a first cell 150 over a left ear, a second cell 150 over a left eye, a third cell 150 over a right eye and a fourth cell 150 over a right ear. Because the typical circumferential distance between an average human eye and ear is typically generally about forty to fifty percent greater than the interpupillary distance, it is desirable in one embodiment to increase the spacing between centers of adjacent cells 150 somewhat to allow the cells 150 in a series of four to conveniently fit over eyes of a wearer as well as over ears of a wearer. To accommodate such a positioning of the sleeve, the spacing between centers of adjacent cells 150 is preferably between about 80 millimeters and about 100 millimeters. As it is not critical that the centers of cells 150 rest directly over centers of eyes of a wearer, having this spacing between adjacent cells 150 slightly greater than the interpupillary distance merely causes the cells placed over the eyes of the wearer to extend somewhat laterally more than is necessary so that the next adjacent cells can rest over ears of the wearer.

The sleeve 140 in the embodiment of FIGS. 8-10 is shown completely without an attached pillowcase. However, the proximal end can be fitted with a fastener of some type which can allow for attachment to a complementally configured pillowcase and/or pillow. For instance, the proximal end of the sleeve 140 can be fitted with buttons, snaps, zippers or other fasteners for attachment to a suitably configured edge of a pillowcase or pillow. This fastener is typically a removably attachable fastener so that the sleeve 140 can be utilized both with and without the pillow and/or pillowcase.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An eye covering, comprising in combination:
an elongate flexible sleeve having a hollow interior;
said sleeve flexible enough to be configured to wrap around a majority of a head of a wearer and against the head of the wearer;
said sleeve having an elongate form between a proximal end and a distal end;
said distal end and said proximal end free from coupling to other structures; and
said interior at least partially filled with a plurality of individual beads of media.

2. The eye covering of claim 1 wherein said interior of said sleeve is divided into individual cells, at least some of said cells containing said media to prevent media from moving between at least some of said cells.

3. The eye covering of claim 2 wherein at least one end cell adjacent said proximal end is empty of media.

4. The eye covering of claim 3 wherein said end cell adjacent said proximal end is empty of media and said end cell adjacent said distal end is empty of said media.

5. The eye covering of claim 1 wherein said proximal end of said sleeve is adapted to be removably attachable to a head resting structure.

6. The eye covering of claim 1 wherein said sleeve has a first side opposite a second side, said first side and said second side formed of distinct materials with said material forming said first side and said material forming said second side having distinct heat transfer properties, such that said first side and said second side have a distinct feel when in contact with a wearer.

7. The eye covering of claim 1 wherein said interior of said sleeve is divided into individual cells, at least some of said cells containing said media to prevent media from moving between at least some of said cells; and
wherein said cells are spaced so that centers of said cells which are adjacent to each other are configured to be spaced apart by a distance similar to a distance between average adult human eyes.

8. An eye covering, comprising in combination:
an elongate flexible sleeve having a hollow interior;
said sleeve having an elongate form between a proximal end and a distal end;
said distal end and said proximal end free from coupling to other structures;
said interior at least partially filled with a plurality of individual beads of media;
wherein said interior of said sleeve is divided into individual cells, at least some of said cells containing said media to prevent media from moving between at least some of said cells; and wherein said cells are spaced so that centers of said cells which are adjacent to each other are configured to be spaced apart by a distance similar to a distance between average adult human eyes.

9. The eye covering of claim 8 wherein said cells have centers spaced between 60 millimeters and 70 millimeters from each other.

10. The eye covering of claim 8 wherein adjacent said cells are spaced apart by a distance such that centers of adjacent cells are configured to be spaced by an amount similar to a distance between average human eyes and ears.

11. The eye covering of claim 10 wherein adjacent said cells have centers spaced from each other by an amount between about 60 millimeters and about 100 millimeters.

12. The eye covering of claim 8 wherein said sleeve has a first side opposite a second side, said first side and said second side formed of distinct materials with said material forming said first side and said material forming said second side having distinct heat transfer properties, such that said first side and said second side have a distinct feel when in contact with a wearer.

13. The eye covering of claim 8 wherein said sleeve has a perimeter which includes at least one nose notch defining a lesser height region of said sleeve than portions of said sleeve on either side of said nose notch.

14. An eye covering, comprising in combination:
an elongate flexible sleeve having a hollow interior;
said sleeve having an elongate form between a proximal end and a distal end;
said distal end and said proximal end free from coupling to other structures;
said interior at least partially filled with a plurality of individual beads of media;
wherein said sleeve has a first side opposite a second side, said first side and said second side formed of distinct materials with said material forming said first side and said material forming said second side having distinct heat transfer properties, such that said first side and said second side have a distinct feel when in contact with a wearer; and
said sleeve having a perimeter which includes at least one nose notch defining a lesser height region of said sleeve than portions of said sleeve on either side of said nose notch.

15. The eye covering of claim 14 wherein said first side and said second side have different heat capacities.

16. The eye covering of claim 14 wherein said first side and said second side have different coefficients of heat transfer.

17. The eye covering of claim 14 wherein said first side and said second side have different texture.

18. The eye covering of claim 14 wherein said first side and said second side have different porosity.

19. The eye covering of claim 14 wherein said interior of said sleeve is divided into individual cells, at least some of said cells containing said media to prevent media from moving between at least some of said cells; and
wherein said cells are spaced so that centers of said cells which are adjacent to each other are configured to be spaced apart by a distance similar to a distance between average adult human eyes.

20. The eye covering of claim 14 wherein said sleeve has a perimeter which includes at least one nose notch defining a lesser height region of said sleeve than portions of said sleeve on either side of said nose notch.

* * * * *